(12) United States Patent
Chen et al.

(10) Patent No.: US 8,729,335 B2
(45) Date of Patent: May 20, 2014

(54) NRIP KNOCKOUT MICE AND USES THEREOF

(71) Applicant: National Taiwan University, Taipei (TW)

(72) Inventors: Show-Li Chen, Taipei (TW); Hsin-Hsiung Chen, Taipei (TW); Kuan-Liang Lin, Taipei (TW); Wan-Lun Yan, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/689,472

(22) Filed: Nov. 29, 2012

(65) Prior Publication Data
US 2013/0081148 A1    Mar. 28, 2013

Related U.S. Application Data

(63) Continuation-in-part of application No. 12/882,546, filed on Sep. 15, 2010.

(51) Int. Cl.
*A01K 67/027* (2006.01)
*A01K 67/033* (2006.01)
*C12N 15/00* (2006.01)

(52) U.S. Cl.
USPC .................................. 800/18; 800/9; 800/25

(58) Field of Classification Search
USPC .................................................. 800/9, 18, 25
See application file for complete search history.

(56) References Cited

PUBLICATIONS

Picciotto et al. (1998, Physiological Rev., vol. 78(4), pp. 1131-1163).*
Tsai et al. (2005, JBC, vol. 280(20), pp. 20000-20009).*
Zhang et al. (2006, J. Translational Med., vol. 4, pp. 1-12).*
Chen et al. (2008, Nucleic Acid Res., vol. 36(1), pp. 51-66).*
La Spada et al. (1991, Nature, vol. 352, pp. 77-79).*

* cited by examiner

*Primary Examiner* — Anoop Singh
*Assistant Examiner* — David A Montanari
(74) *Attorney, Agent, or Firm* — WPAT, P.C.; Anthony King; Kay Yang

(57) ABSTRACT

The present invention directs to a transgenic NRIP knockout mouse, the genome of which is manipulated to comprise a disruption of a nuclear receptor interaction protein (NRIP) gene, wherein the NRIP gene is disrupted by deletion of exon 2, the mouse exhibits a phenotype comprising abnormal muscular function. The present invention also directs to a method for making a transgenic NRIP knockout mouse whose genome comprises a homozygous disruption of the NRIP gene, the mouse exhibits abnormal muscular function.

8 Claims, 11 Drawing Sheets

FIGURE 2 A
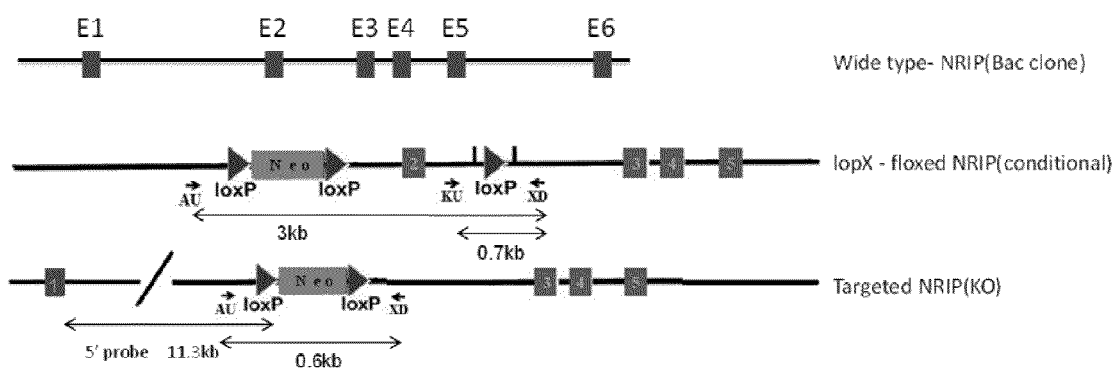
FIGURE 2B
FIGURE 2C
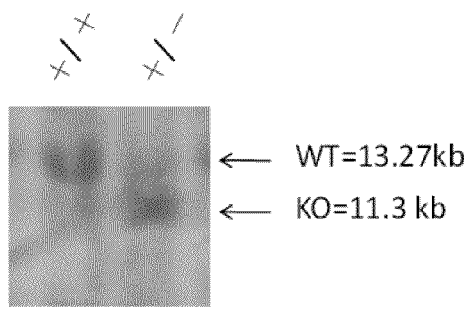
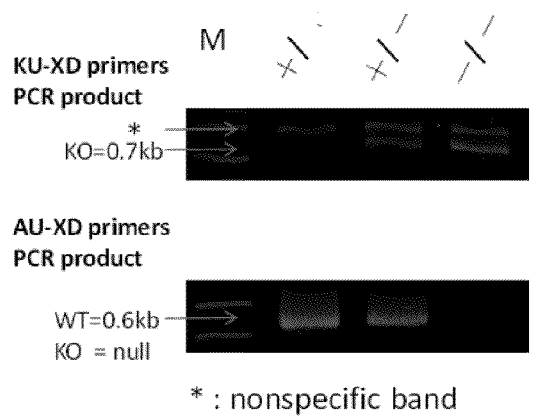

Slow myosin

GAPDH

NRIP KNOCKOUT MICE AND USES THEREOF

CROSS-REFERENCE TO RELATED APPLICATIONS

This application is a Continuation-in-part of the pending U.S. patent application Ser. No. 12/882,546 filed on Sep. 15, 2010.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the prior art of record and any search that the Office deems appropriate.

FIELD OF THE INVENTION

The present invention relates to a transgenic nuclear receptor interaction protein (NRIP) knockout mouse with a phenotype comprising abnormal muscular function. The present invention also relates to a method for making of a transgenic NRIP knockout mouse.

DESCRIPTION OF PRIOR ART

The muscular dystrophies are a group of clinically and genetically heterogeneous disorders of the skeletal muscle inherited in either autosomal dominant or recessive fashion. Muscular dystrophies are characterized clinically by progressive muscle weakness predominantly in the pelvic and shoulder-girdle muscles, serum creatine kinase (SCK) elevation, normal intelligence and great variability, ranging from severe forms with onset in the first decade and rapid progression to milder forms with later onset and a slower course (Tsai, T. C. et al, *J. Biol. Chem.*, 2005, 280, 20000-20009). The diagnosis of muscular dystrophies can be excluded by the finding of severely abnormal dystrophin staining on muscle biopsies. Although analysis of the defective proteins has shed some light onto their functions implicated in the etiology of muscular dystrophies, our understanding of the molecular mechanisms underlying muscular dystrophy remains incomplete.

Skeletal muscles are a mosaic of slow and fast twitch myofibers. Calcium ($Ca^{2+}$) plays a key role in skeletal muscle contraction both in slow and fast fibers and regulates myosin heavy chain isoforms' gene expression. Now, slow myosin fiber is clearly reportedly regulated by the increased intracellular $Ca^{2+}$. Additionally, testosterone increases the intracellular $Ca^{2+}$ level. Nuclear receptor interaction protein (NRIP) is a transcription cofactor, it contains 860 amino acids and seven copies of WD40 domains, and its expression is restricted to the cell nucleus. NRIP is an androgen receptor (AR)-interacting protein to enhance AR-mediated gene expression, it plays a feed-forward role in enhancing the AR-driven NRIP promoter activity via stabilization of the AR protein (Pei-Hong Chen et al, *Nucleic Acids Research*, 2008, Vol. 36, No. 1 51-66). NRIP enhances transcriptional activity of either AR or GR (glucocorticoid receptors) via ligand-dependent interactions (Tsai, T. C. et al, *J. Biol. Chem.*, 2005, 280, 20000-20009).

In the recent report, the clinical gene expression profiles of muscular dystrophy patients lack NRIP gene expression by microarray assay. According to the analysis of differentially expressed genes between relative normal and dystrophic muscles from the same Limb-girdle muscular dystrophy (LGMD) patient, NRIP expression pattern was down-regulated in the muscular dystrophy patient (Yong Zhang et al, *Journal of Translational Medicine*, 2006, 4:53). However, the relation of NRIP caused muscular dystrophy needs to be further investigated.

BRIEF DESCRIPTION OF THE DRAWINGS

FIG. 1A shows that the IQ domain (SEQ ID NO: 7) of NRIP protein (SEQ ID NO: 6) locates on amino acid 691 to 713. The arrows indicate the highly conserved positions of amino acid compared with the other proteins containing IQ domain reported previously. The internal IQ-deleted mutant form of NRIP is generated by site-directed mutagenesis; and named NRIPΔIQ.

FIG. 1B shows that NRIP interacts with $Ca^{2+}$/CaM in vitro. The NRIP proteins from in vitro translation (upper panel) or bacterially expressed (His-NRIP, lower panel) are incubated with CaM-agarose in the buffer containing calcium ions or EGTA. The proteins binding to CaM are then eluted by using EGTA-containing buffer and analyzed with anti-NRIP antibody. The data indicate that NRIP binds to CaM in the presence of calcium.

FIG. 1C shows that IQ domain of NRIP is responsible for $Ca^{2+}$/CaM binding. The equal amounts of in vitro translated wt NRIP and IQ-deleted NRIP proteins of NRIPΔIQ are incubated with CaM-agarose. The CaM-binding proteins are then analyzed by western-blotting with anti-NRIP antibody.

FIG. 1D shows that NRIP interacts with $Ca^{2+}$/CaM in vivo. The 293T cells are transiently co-transfected with NRIP-FLAG and CaM conjugates with EGFP expression plasmids. After 48 h, the cell lysates are collected and immunoprecipitated with anti-FLAG or anti-EGFP for NRIP and CaM, respectively. The immunoprecipitated proteins are then subjected to western-blotting with antibodies indicated.

FIGS. 2A-2E show generation of NRIP knockout mice.

FIG. 2A shows schematic illustration of genomic structure of the NRIP wild-type, NRIP flox, and NRIP-deleted alleles.

FIG. 2B shows southern blot hybridization of mouse tail genomic DNA isolated from wild-type (+/+) and heterozygous (+/−) offspring of heterozygous intercross. After restriction enzyme Sca I digestion and DNA denaturation, the genomic DNA is hybridized by 5' flanking probe designed on NRIP intron 1 region. The wild-type allele represents a band on the size of 13.27 kb and the NRIP knockout allele represents a band on the size of 11.3 kb.

FIG. 2C shows genome typing of mouse tail DNA from wild-type (+/+), heterozygous (+/−) and homozygous (−/−) offspring by PCR analysis. The result shows a targeted product of 0.7 kb detected by AU-XD primers, and a wild-type product of 0.6 kb detected by KU-XD primers (*: nonspecific band).

FIG. 2D shows expression of NRIP mRNA level in NRIP knockout mice by RT-PCR analysis. The upper panel shows the schematic illustration of the designed primers to detect the deletion of NRIP exon 2; the lower panel shows RT-PCR analysis of NRIP mRNA isolated from testis, heart and skeletal muscle of wild-type (WT) and knockout (KO) offspring. β-actin or GAPDH was examined as a loading control.

FIG. 2E shows expression of mouse NRIP protein in wild-type (WT) and knockout (KO) adult tissues. Following tissue dissection and protein extraction, expression of NRIP is analyzed by Western blot with primary NRIP antibody. The size of NRIP protein is examined by knockdown of NRIP expression in LNCap human prostate cancer cell line (as a positive control). GAPDH is examined as a loading control. The left panel shows the expression of NRIP in WT and KO skeletal muscle tissue; the right panel shows the expression of NRIP and androgen receptor (AR) in WT and KO testis tissue.

FIG. 3A shows western blot analysis of NRIP expression, using total protein (100 μg) from the hindlimb skeletal muscle tissues of adult (10-week) male mice.

FIG. 3B shows analysis of slow myosin (MHC7) expression in soleus and gastrocnomius (Gast.) muscle tissues respectively.

The size of NRIP protein is examined by knockdown of NRIP expression in LNCap human prostate cancer cell line. The GAPDH serves as an internal control for protein loading.

Figure 3A:
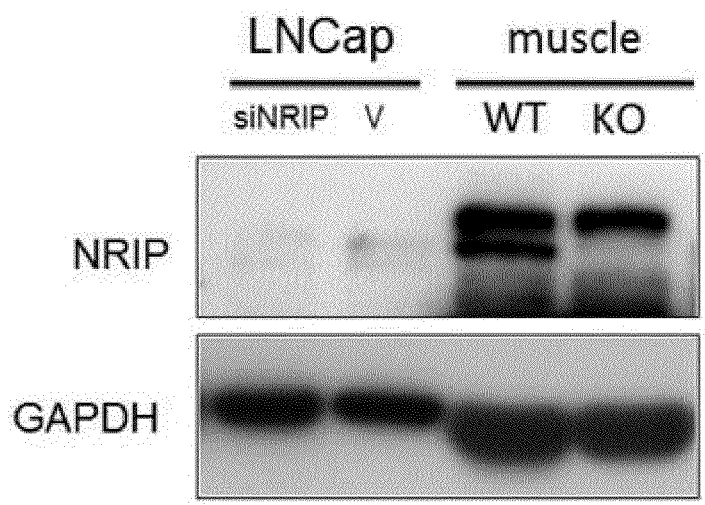
FIGS. 3A-3B show expression of NRIP and slow myosin in skeletal muscle tissues of adult male mice (Following the tissue dissection and protein extraction).
Figure 3B:
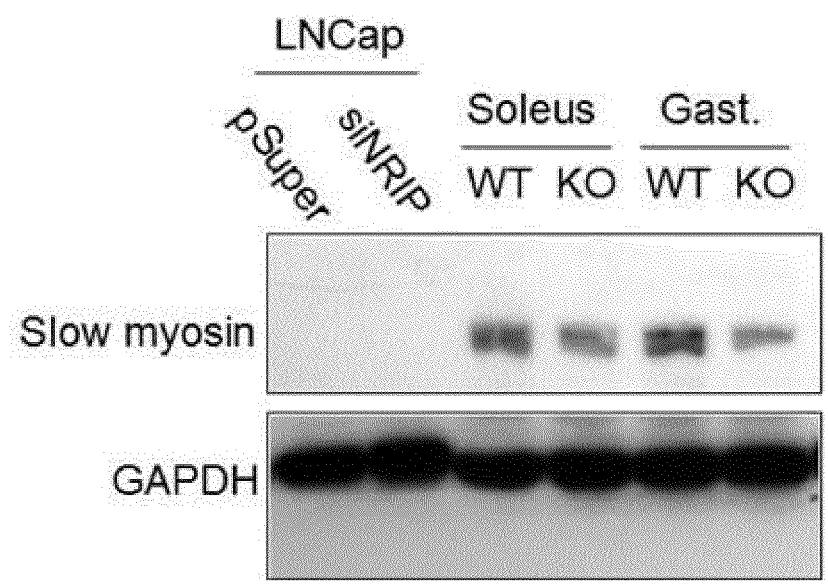
Figure 4:
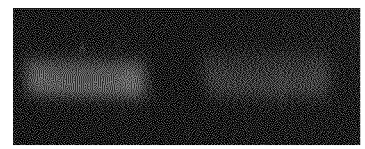
Figure 4:
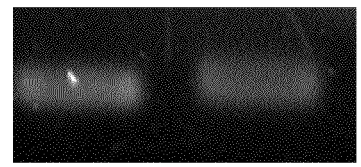

FIG. 4 shows RNA expression of slow myosin in soleus muscle tissues. As described tissues from FIG. 3, RNA is extracted and analyzed for the gene expression of slow myosin (MHC7).

Figure 5:
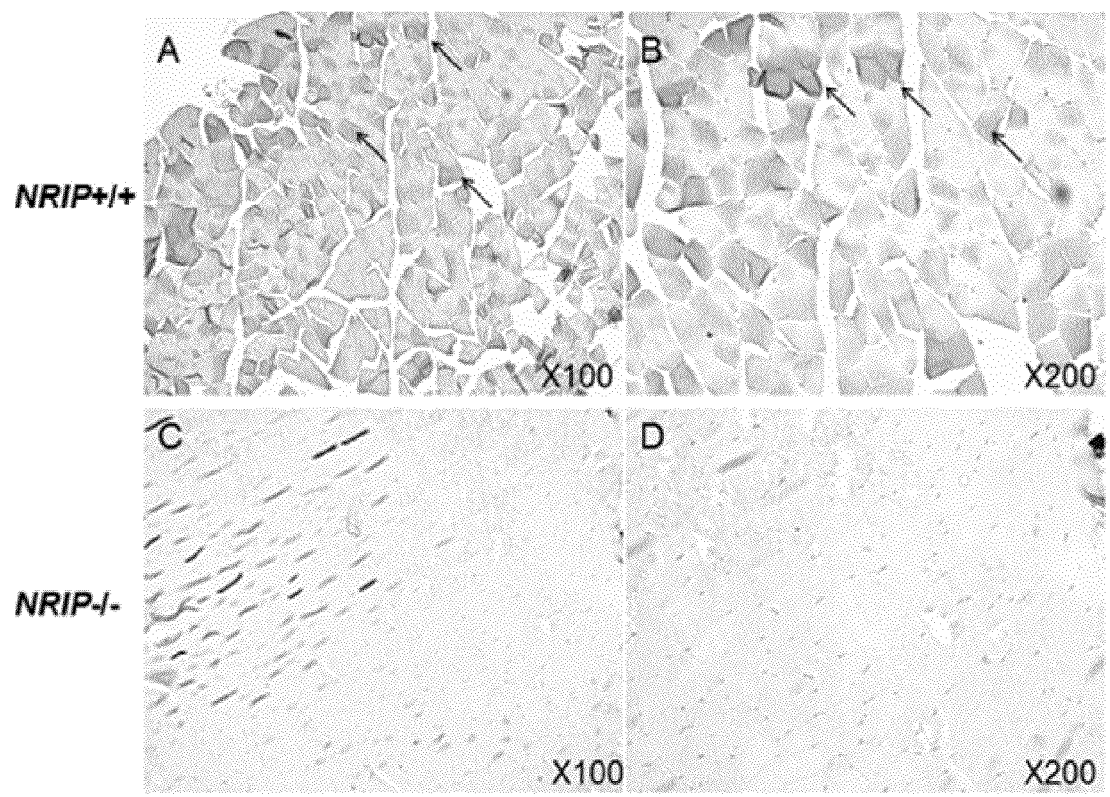

FIG. 5 shows immunohistochemistry analysis of slow myosin expression in gastrocnomius skeletal muscle tissue of 12-week old NRIP$^{+/+}$ and NRIP$^{-/-}$ mice. Following tissue dissection and paraffin embedding, the 4 μm sections are incubated with slow myosin primary antibody (MHC 7) for overnight and stained with 3,3' Diaminobenzidine (DAB) chromogen. In wild-type mice (A and B), the slow myosin is expressed dispersedly in gastrocnomius tissue. In NRIP$^{-/-}$ mice (C and D), the slow myosin is less expressed in this tissue. (magnification: A and C X100; B and D X200). Arrow mark: slow myosin.

Figure 6A:
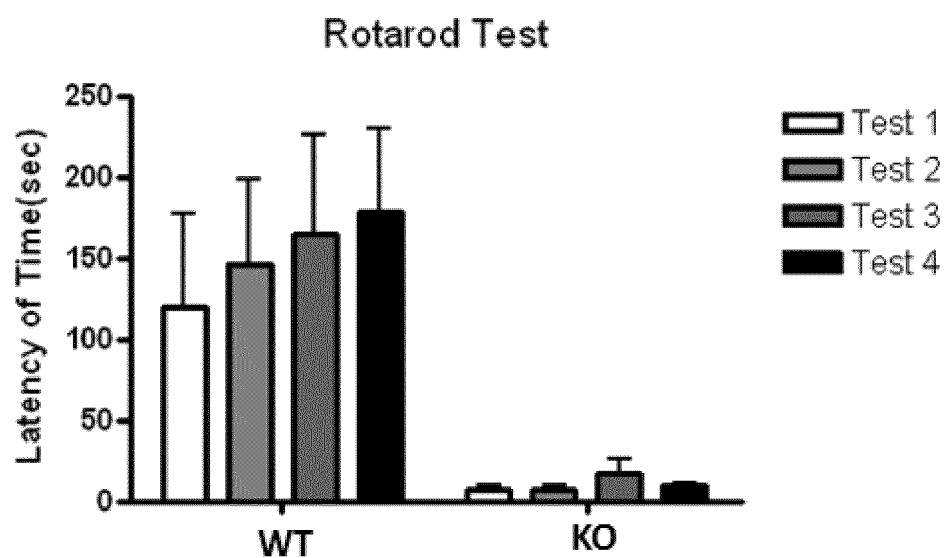
Figure 6B:
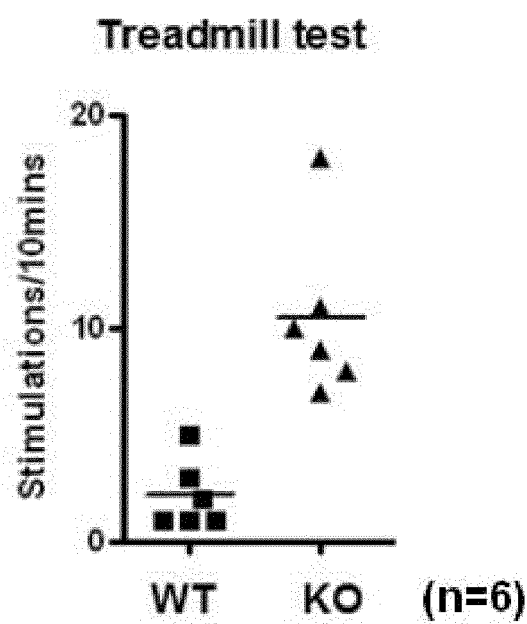

FIGS. 6A-6B show exercise performance of NRIP WT and KO mice.

FIG. 6A shows that NRIP KO (NRIP$^{-/-}$) mice show shorter riding time to stay on a rotating rod in the rotarod test compared to WT (NRIP$^{+/+}$) mice. Mice (8 weeks old) are placed on a rod rotating at 10 r.p.m. and measure their riding time in four trials. A maximum of 5 mins is allowed per trial. *$P<0.05$ by t-test.

FIG. 6B shows the treadmill test. To measure time to running exhaust, mice (8 weeks old) are placed on 5% slope six-lane treadmill at 20 m/min The times of electrical stimulus are recorded as the times they exhaust for running *$P<0.05$ by t-test.

FIGS. 7A-7D show the in vivo maximum contractile force and time to fatigue in NRIP WT and KO mice.

Figure 7A:
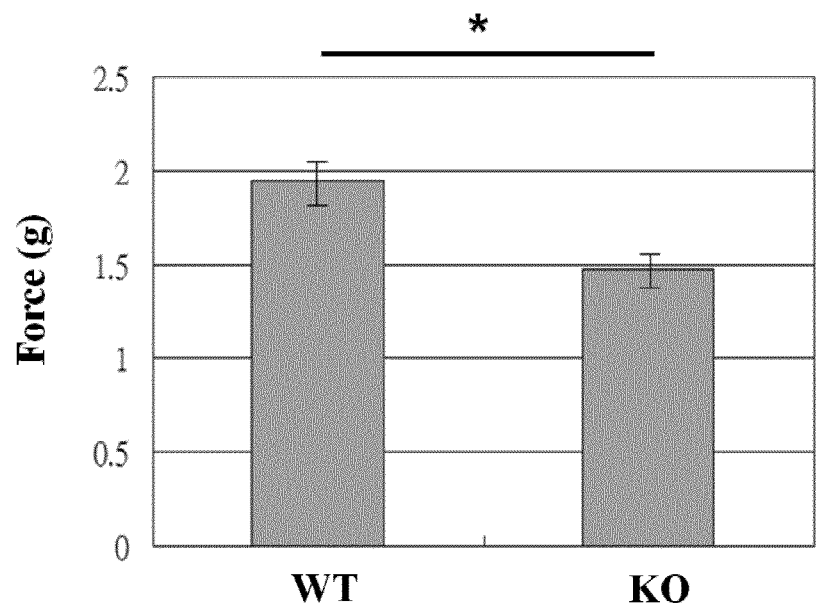

FIG. 7A shows in vivo diaphragm contraction analysis of NRIP WT and KO mice (8-10 weeks old). One of diaphragm is connected to the transducer and directly excited by electric stimulation using a plate electrode. *$P<0.05$ by t-test.

Figure 7B:
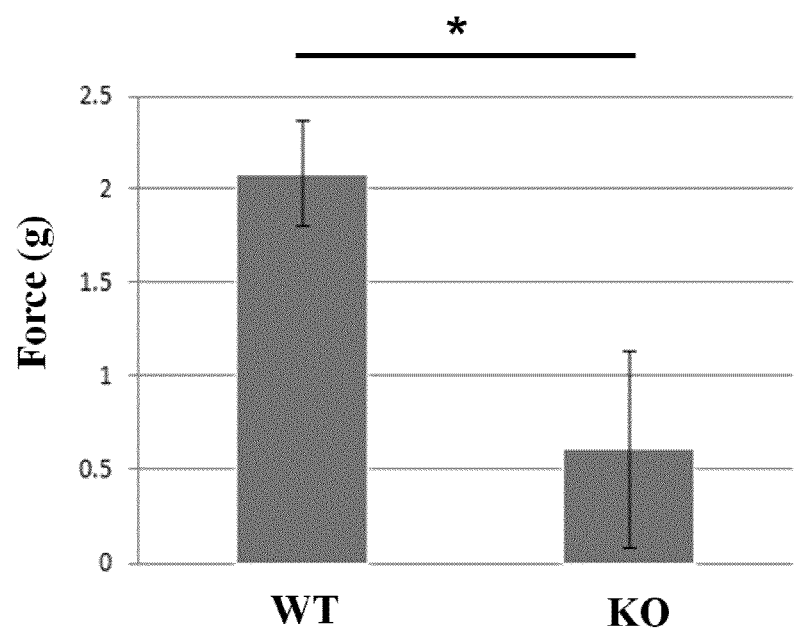

FIG. 7B shows in the treatment of 1 μM d-tubocurarine (d-Tc), the contraction of NRIP KO mice diaphragm are still weaker than the NRIP WT mice.

Figure 7C:
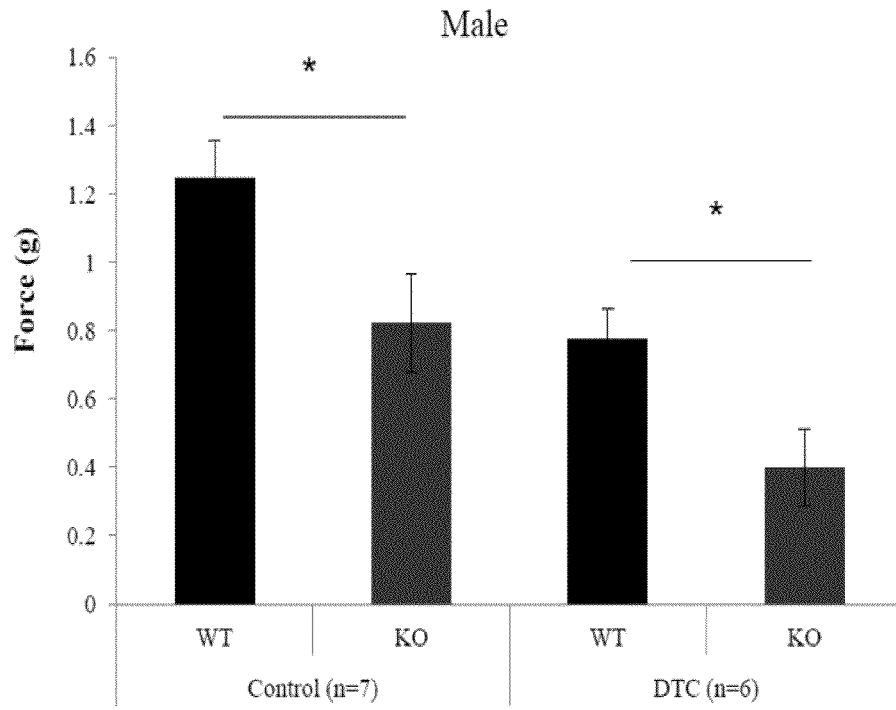

FIG. 7C shows isometric force measurements on isolated soleus muscles from 8-12 weeks old mice. Single twitches are evoked by electrical stimulator (Grass S88) in tyrode solution and in neuromuscular blocking tyrode solution contained 0.1 μnM d-Tc at 37° C. After equilibration for 30-min, muscles are stimulated via plantinum wire electrodes with 5 ms square pulses and 10× threshold at the resting tension (L0) of 1.0 g. NRIP KO mice exhibits reduced contractile force than WT even in the present of acetylcholine receptor antagonist d-Tc.

Figure 7D:
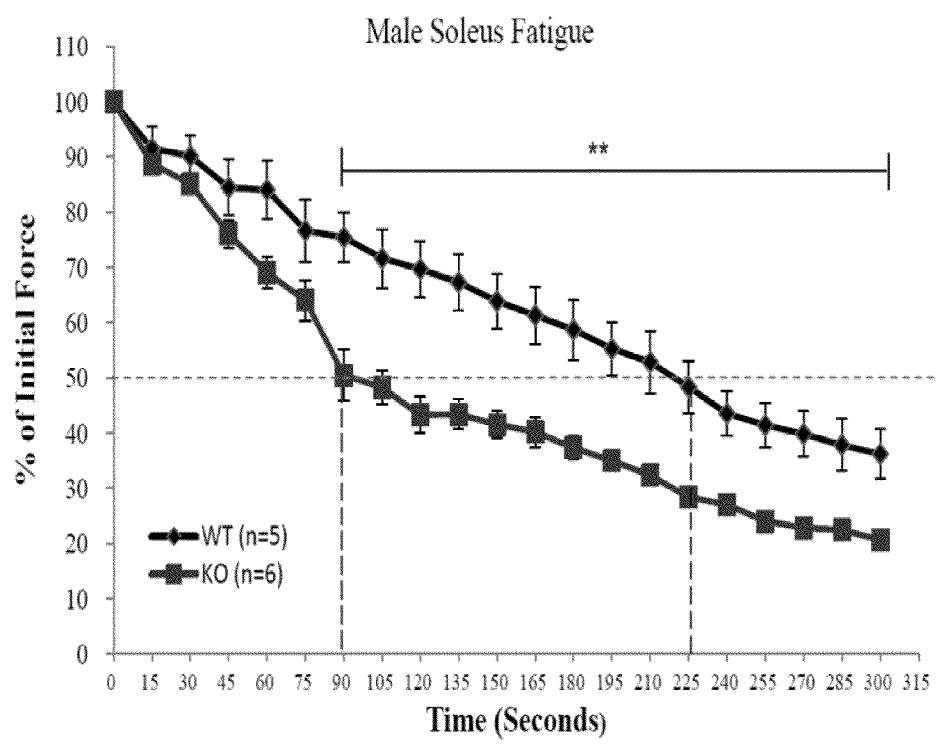

FIG. 7D shows that soleus muscles are fatigued by repetitive stimulation at 100 Hz for 800 ms, once every 5 seconds, for a total 300 seconds. Fatigue is defined as 50% decline of relative force by repetitive stimulation at a given time. *$P<0.05$, **$P<0.01$ by Student's t test.

SUMMARY OF THE INVENTION

The present invention relates to a transgenic NRIP knockout mouse, the genome of which is manipulated to comprise a disruption of a nuclear receptor interaction protein (NRIP) gene, wherein the NRIP gene is disrupted by deletion of exon 2, the knockout mouse exhibits a phenotype comprising abnormal muscular function.

The present invention also relates to a method for making a transgenic NRIP knockout mouse whose genome comprises a homozygous disruption of the NRIP gene, the method comprising the steps of: (a) transfecting a mouse embryonic stem cell with a nucleic acid comprising the homozygous disruption of NRIP gene, wherein the NRIP gene is disrupted by deletion of exon 2; (b) selecting the transgenic embryonic stem cell that have incorporated said nucleic acid into their genome; (c) introducing at least one of the transgenic embryonic stem cell into an embryo to produce a chimeric mouse comprising the transgenic embryonic stem cells; (d) breeding the chimeric mouse with a wild type mouse to obtain F1 progeny that are heterozygous for a disrupted NRIP gene; and (e) breeding a male mouse of said F1 progeny with a female mouse of said F1 progeny to obtain F2 progeny that are homozygous for the disrupted NRIP gene, wherein the knockout mouse exhibits abnormal muscular function.

DETAILED DESCRIPTION OF THE INVENTION

A "knockout mouse" (or "KO mouse") is a mouse in the genome of which a specific gene has been inactivated by the method of gene targeting. A knockout mouse can be a heterozygote (i.e., one defective/disrupted allele and one wild-type allele) and a homozygote (i.e., two defective/disrupted alleles). "Knockout" of a target gene means an alteration in the sequence of the gene that results in a decrease or, more commonly, loss of function of the target gene, preferably such that target gene expression is undetectable or insignificant. A knockout of an NRIP gene means that function of the NRIP gene has been substantially decreased or lost so that NRIP expression is not detectable (or may only be present at insignificant levels). The term "knockout" is intended to include partial or complete reduction of the expression of at least a portion of a polypeptide encoded by the targeted endogenous gene (here NRIP) of a single cell, a population of selected cells, or all the cells of a mammal.

As used herein, "NRIP" refers to a protein or a nucleic acid encoding the protein. A "gene" refers to the smallest, independently functional unit of genetic material that can code for and drive the expression of a protein, e.g., NRIP, or whose presence or absence has a phenotypic consequence on a cell or organism. The term "the expression level of NRIP", as used herein, refers to the expression level of protein, RNA or DNA of NRIP. The NRIP gene, as used herein, is SEQ ID NO: 1. The exon 2, as used herein, is SEQ ID NO: 2.

The present invention provides a transgenic knockout mouse whose genome comprises a homozygous disruption of a nuclear receptor interaction protein (NRIP) gene, wherein the NRIP gene is disrupted by deletion of exon 2, and said knockout mouse exhibits a feature comprising abnormal muscular function. In a preferred embodiment, the transgenic knockout mouse exhibits lower or no expression level of NRIP as compared to a wild type mouse. In accordance with the present invention, the NRIP is $Ca^{2+}$-dependent calmodulin binding protein which modulates the expression of slow myosin. In a preferred embodiment, the transgenic knockout mouse exhibits the decreased expression level of slow myosin as compared to a wild type mouse. Because the NRIP transgenic knockout mouse shows lower expression level of slow myosin, it causes the abnormal muscle function such as but not limited to reduction in hindlimb muscles contraction. In a preferred embodiment, the abnormal muscular function is muscle dystrophy.

The present invention also provides a method of making the transgenic knockout mouse described above, said method comprising: (a) transfecting a mouse embryonic stem cell with a nucleic acid comprising the homozygous disruption of NRIP gene, wherein the NRIP gene is disrupted by deletion of exon 2; (b) selecting transgenic embryonic stem cells that have incorporated said nucleic acid into their genome; (c) introducing at least one of the transgenic embryonic stem cells into an embryo to produce a chimeric mouse comprising at least one of the transgenic embryonic stem cells; (d) breeding the chimeric mouse with a wild type mouse to obtain F1 progeny that are heterozygous for a disrupted NRIP gene; and (e) breeding a male mouse of said F1 progeny with a female mouse of said F1 progeny to obtain F2 progeny that are homozygous for the disrupted NRIP gene, wherein the knockout mouse exhibits a feature comprising abnormal muscular function. The homozygous disruption of NRIP gene in the embryonic stem cells refers to modification of the NRIP gene in manner which decreases or prevents expression of NRIP gene and its product in the cell. When using the transgenic embryonic stem cells to produce a knockout mouse, the functional disruption of NRIP gene expresses in the mouse. In a preferred embodiment, the transgenic knockout mouse exhibits lower or no expression level of NRIP as compared to a wild type mouse. In accordance with the present invention, the expression level of slow myosin is affected by the NRIP gene. In one embodiment, the transgenic knockout mouse exhibits decreased expression level of slow myosin as compared to a wild type mouse. The expression of slow myosin is declined that induces the abnormal muscular function of NRIP knockout mouse. In a preferred embodiment, the abnormal muscular function is muscle dystrophy.

EXAMPLES

The examples below are non-limiting and are merely representative of various aspects and features of the present invention.

Example 1

NRIP Binds Calmodulin In Vitro and In Vivo

Figure 1A:
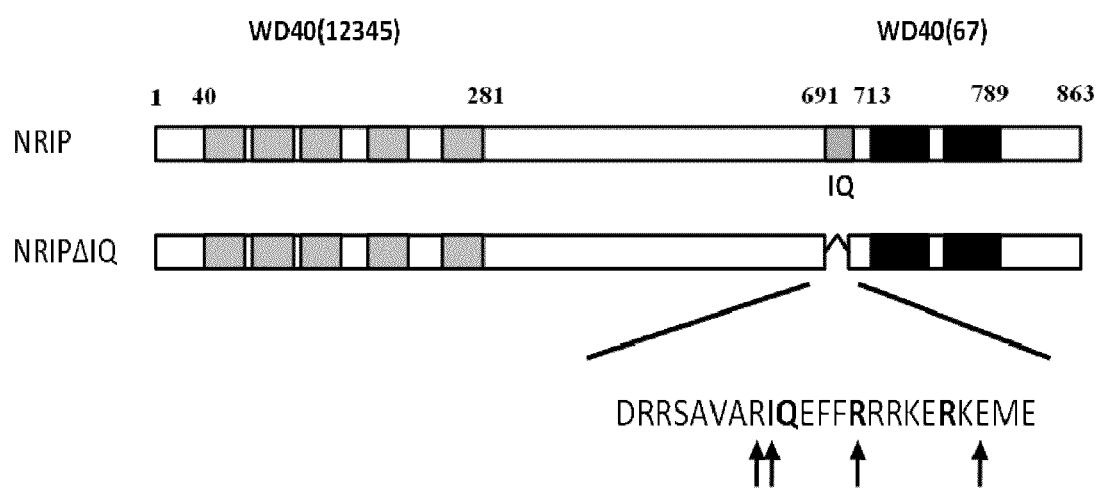
FIGS. 1A-1D show that NRIP binds calmodulin in vivo and in vitro.
Figure 1B:
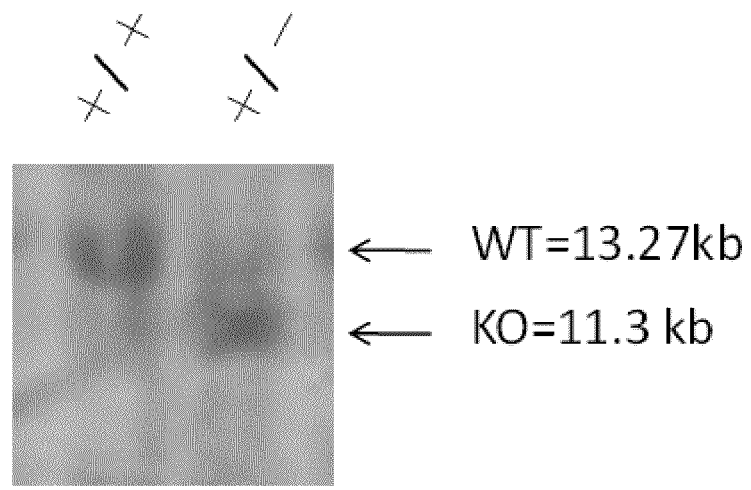
Figure 1C:
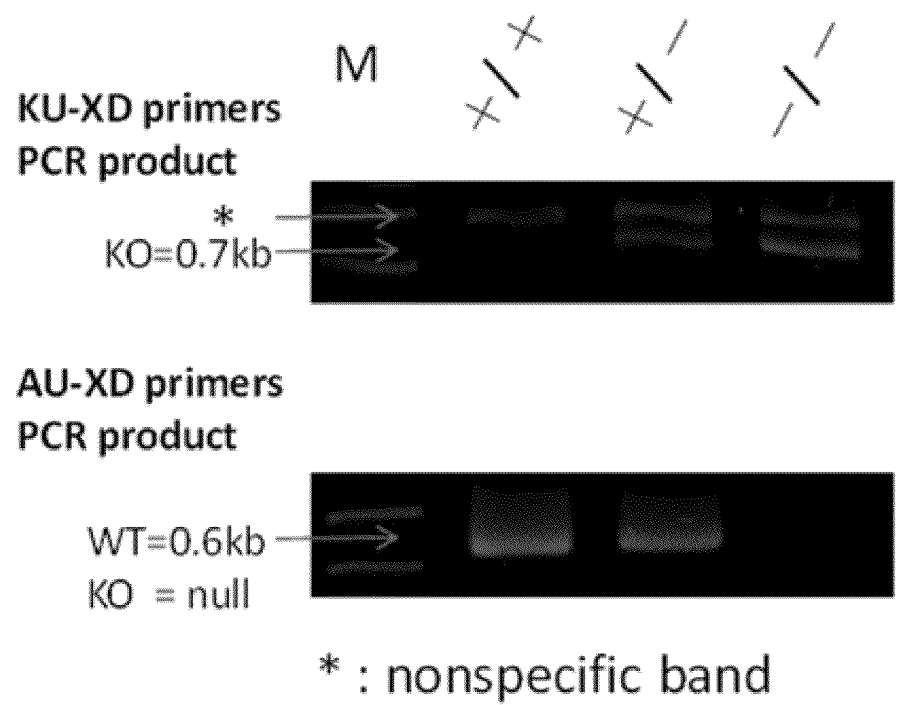
Figure 1D:
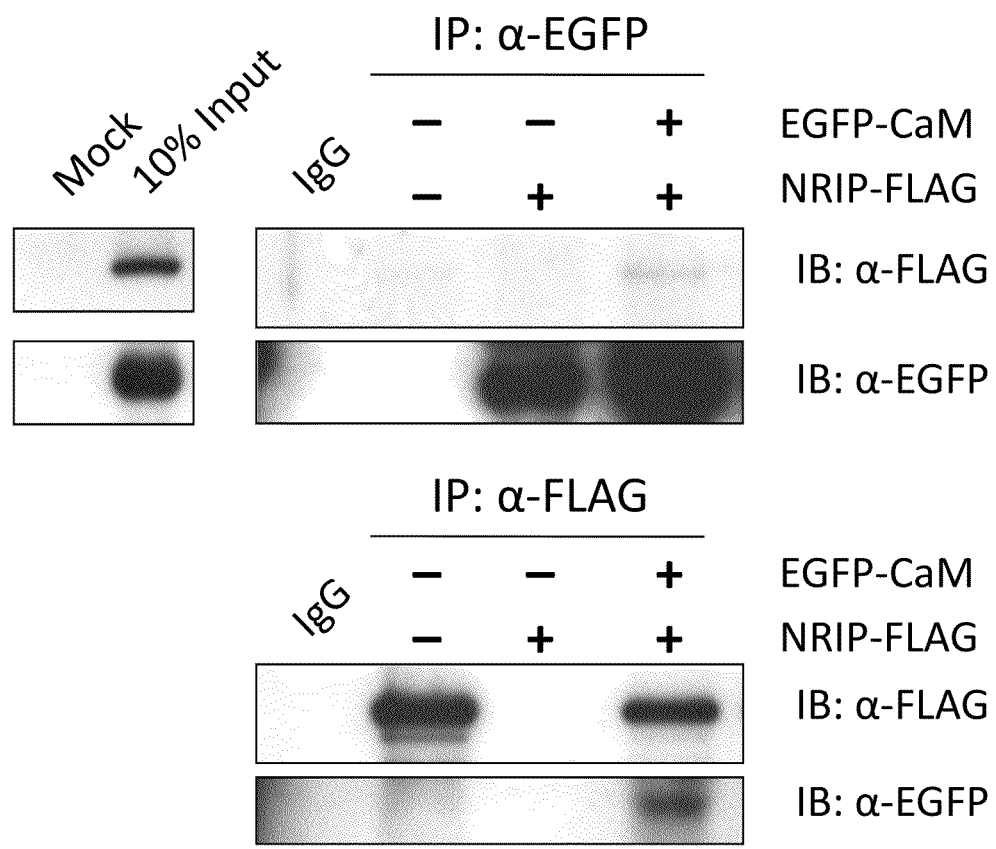

The wild-type NRIP proteins (SEQ ID NO: 6) and IQ domain (SEQ ID NO: 7)-deleted NRIP proteins from in vitro translation or bacterially expressed His-NRIP were incubated with CaM-agarose. The proteins bound to CaM were then eluted by using EGTA-containing buffer and analyzed with anti-NRIP antibody. These data indicated that NRIP bound to CaM in the presence of calcium (FIG. 1B and FIG. 1C). To test the NRIP that could interact with CaM in vivo, the 293T cells were transiently co-transfected with NRIP-FLAG and CaM conjugated with EGFP expression plasmids. After 48 h, the cell lysates immunoprecipitated with anti-FLAG or anti-EGFP for NRIP and CaM, respectively and then analyzed with immunoblot (FIG. 1D). The results showed that NRIP interacts with CaM.

Example 2

Generation of NRIP Knockout Mice

Figure 2D:
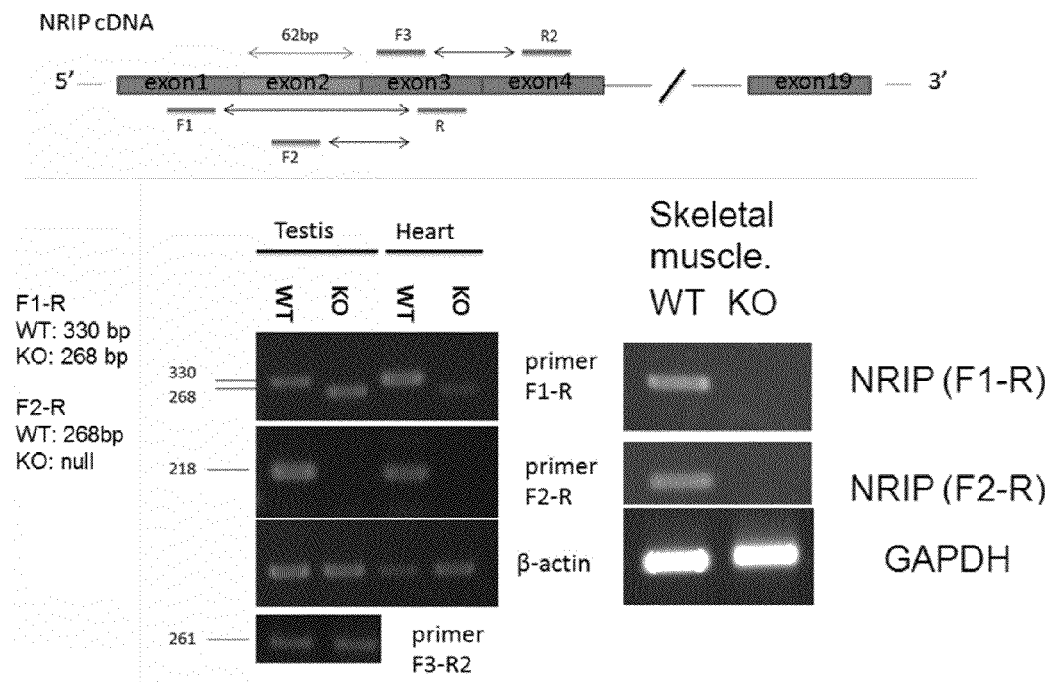
Figure 2E:
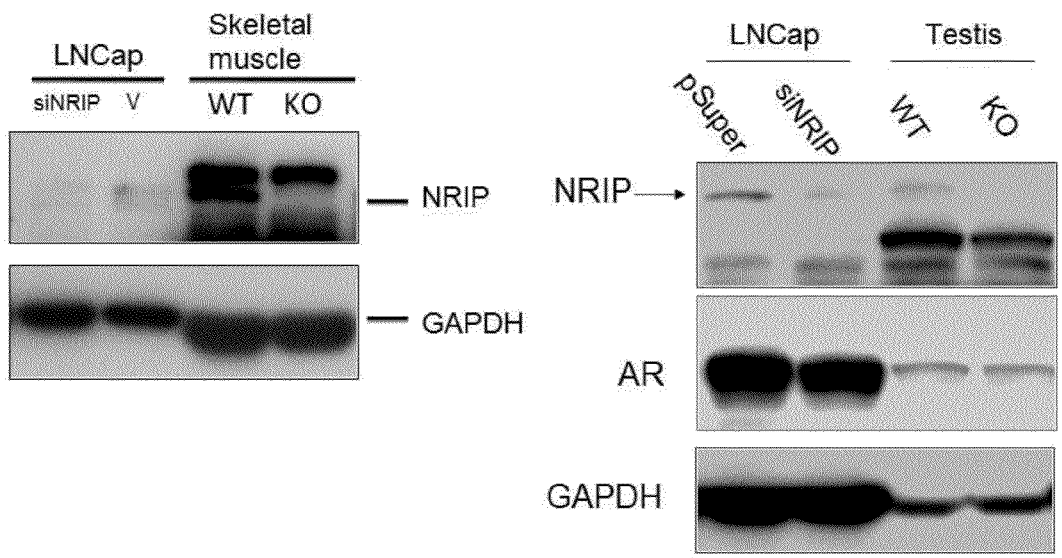

The loxP-floxed NRIP conventional knockout mice were suitable for investigating the role of NRIP in skeletal muscle development. The NRIP exon 2 was deleted after loxP site recombination (FIG. 2A). The genome NRIP deletion was confirm by Southern blot (FIG. 2B) and mouse tail genometyping (FIG. 2C), respectively. The present invention also detected the expression of NRIP mRNA in the testis, heart and skeletal muscle tissues. The results showed that the exon2 deleted NRIP was detected by the designed F1-R primers and was not detected by the designed F2-R primers (FIG. 2D). The expression of NRIP protein in testis and skeletal muscle tissue was also performed by Western blot, in this result, the NRIP was expressed in the wild-type mouse testis and skeletal muscle tissues but not in NRIP-null mouse testis and skeletal muscle tissues (FIG. 2E).

Example 3

Expression of NRIP and Slow Myosin in Skeletal Muscle of Adult Male Mice

The previous results showed that the NRIP can bind to CaM. Besides, the expression of slow myosin was controlled by the $Ca^{2+}$/CaM signaling pathway. Hence, the present invention next investigated the expression of slow myosin in NRIP wild-type and null mice. The present invention dissected the mouse soleus and gastrocnomius muscle tissue and the protein was extracted by RIPA buffer. The slow myosin and NRIP protein expression was performed by the Western blot. The results showed that the expression of slow myosin was decreased in NRIP null mice (FIG. 3B). The expression of NRIP mRNA was also decreased in NRIP null mice (FIG. 4). Moreover, the present invention also examined the expression of NRIP protein in gastrocnomius skeletal muscle tissues by IHC analysis, the result showed that the expression of NRIP was dromatically decreased in NRIP null mice (FIG. 5).

Example 4

Production of NRIP Knockout Mice

NRIP gene comprised SEQ ID NO: 1. NRIP conventional knockout mice were generated by replacing approximately 19.2 kb of genomic sequence that included neomycin resistance gene (Neo). The exon 2 (SEQ ID NO: 2) of NRIP gene was deleted after loxP site recombination (FIG. 2A). Murine NRIP genomic DNA clones were isolated from a 129/SvJ mouse library by using by using a human NRIP cDNA probe. The targeting construct was made by replacing a 19.2 kb containing 1.1 kb neomycin resistance gene cassette in the same orientation as the endogenous NRIP. Linearized targeting construct was electroporated into embryonic stem cells, and G418-resistant clones were selected. Homologous recombinant clones were identified by Southern blot analysis and then injected into C57BL/6 blastocysts. The present invention designed three primers consisting of AU primer (SEQ ID NO: 3), KU primer (SEQ ID NO: 4) and XD primer (SEQ ID NO: 5) to detect mouse tail genometyping. The result showed a targeted product of 0.7 kb detected by AU-XD primers and a wild-type product of 0.6 kb detected by KU-XD primer (FIG. 2C). Male chimera mice were bred to C57BL/6 or 129/Sv females to generate F1 $NRIP^{+/-}$ offsprings. Brother and sister matings were carried out to obtain $NRIP^{-/-}$ mice.

Example 5

NRIP Regulates Muscle Contraction

The present invention investigated the exercise performance of NRIP WT ($NRIP^{+/+}$) and KO ($NRIP^{-/-}$) mice by rotarod and treadmill tests. The mice (8 weeks old) were placed on a rod rotating at 10 r.p.m. and measured their riding time in four trials. A maximum of 5 mins was allowed per trial. The NRIP KO mice showed shorter riding time to stay on a rotating rod in the rotarod test compared to WT mice (FIG. 6A). In the treadmill test, mice (8 weeks old) were placed on 5% slope six-lane treadmill at 20 m/min and measured the time to running exhaust. The times of electrical stimulus were recorded as the times they exhaust for running The results indicated that NRIP KO needed more stimulation times for continuous running within 10 minutes than NRIP WT mice (FIG. 6B). The above results showed that NRIP$^{-/-}$ mice exhibit decreased exercise performance.

Moreover, the present invention investigated that NRIP$^{-/-}$ hindlimb muscles exhibited weaker contractile force. The slow-twitch soleus muscles and diaphragm were isolated from male NRIP$^{+/+}$ and NRIP$^{-/-}$ mice to assess the maximal isometric forces following direct electrical stimulation (single twitch: 1 Hz, square pulses of 5 ms duration and 50 volts) of the muscle in vitro. Besides, the neuromuscular blocker d-tubocurarine (dTC) which was acetylcholine receptor antagonists was contained in tyrode solution to exclude possible neuromuscular transmission effect on muscle contractile activity. In the present of 0.1 μM d-tubocurarine, NRIP$^{-/-}$ muscles exhibited the reduction in maximal force output of single twitch compared with NRIP$^{+/+}$ littermates (FIGS. 7A, 7B and 7C). The results indicated NRIP$^{-/-}$ muscles had weaker muscle strength compared to wild type controls.

Next, the soleus muscles were measured for fatigue resistance by repetitive stimulation at 100 Hz for 800 ms, intervened every 5 seconds, for a total of 300 seconds to assay muscle endurance. Muscle fatigue was defined as a decline in force generating capacity during sustained activity. Here, fatigue was defined as 50% decline of initial force by repetitive stimulation at a given time. The time-to-fatigue for male NRIP$^{-/-}$ muscles was faster than WT mice (FIG. 7D). The length of time for muscle strength of male NRIP$^{+/+}$ controls fell to 50% of initial force was 225 seconds, whereas NRIP$^{-/-}$ muscles only lasted for 90 seconds. The results indicated loss of muscle endurance in male NRIP$^{-/-}$ mice.

One skilled in the art readily appreciates that the present invention is well adapted to carry out the objects and obtain the ends and advantages mentioned, as well as those inherent therein. The animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

---

What is claimed is:

1. A transgenic knockout mouse whose genome comprises a homozygous disruption in its endogenous nuclear receptor interaction protein (NRIP) gene, said disruption comprising a deletion of exon 2 of the NRIP gene which prevents expression of the NRIP protein, wherein said knockout mouse exhibits decreased muscle contractile force and decreased expression of slow myosin as compared to a wild-type mouse.

2. The transgenic knockout mouse of claim 1, wherein the NRIP gene is encoded by the nucleic acid sequence of SEQ ID NO: 1.

3. The transgenic knockout mouse of claim 1, wherein the exon 2 is encoded by the nucleic acid sequence of SEQ ID NO: 2.

4. The transgenic knockout mouse of claim 1, which exhibits lower or no expression of NRIP as compared to a wild type mouse.

5. A method of making a transgenic knockout mouse of claim 1, said method comprising:
   a. transfecting a mouse embryonic stem cell with a nucleic acid comprising the homozygous disruption of NRIP gene, wherein the NRIP gene is disrupted by deletion of exon 2;
   b. selecting the transgenic embryonic stem cell that have incorporated said nucleic acid into their genome;
   c. introducing at least one of said transgenic embryonic stem cell into an embryo to produce a chimeric mouse comprising the transgenic embryonic stem cells;
   d. breeding said chimeric mouse with a wild type mouse to obtain F1 progeny that are heterozygous for a disrupted NRIP gene; and
   e. breeding a male mouse of said F1 progeny with a female mouse of said F1 progeny to obtain F2 progeny that are homozygous for its disrupted endogenous NRIP gene, wherein said knockout mouse exhibits decreased muscle contractile force and a decreased expression of slow myosin as compared to a wild-type mouse.

6. The method of claim 5, wherein the NRIP gene is encoded by the nucleic acid sequence of SEQ ID NO: 1.

7. The method of claim 5, wherein the exon 2 is encoded by the nucleic acid sequence of SEQ ID NO: 2.

8. The method of claim 5, wherein the knockout mouse exhibits lower or no expression of NRIP as compared to a wild type mouse.

* * * * *

SEQUENCE LISTING

```
<160> NUMBER OF SEQ ID NOS: 7

<210> SEQ ID NO 1
<211> LENGTH: 3306
<212> TYPE: DNA
<213> ORGANISM: Mus musculus
<220> FEATURE:
<221> NAME/KEY: misc_feature
<222> LOCATION: (1)..(3306)

<400> SEQUENCE: 1
atgttctggg tagtctgagg agagtatgag gcgagccgtg gcccgggtac ctctccgctc      60
ccggggagaa ggcgcggccg tggctgccgc cctctgagtc gcggcgccgg cgaggccccg     120
gggcgcgcgc atggtgctgg tgccgctcgg gtgttgatcg gcctgtcccc tccctctctt     180 ccctcccca cccccgcgg tggtctcccc tttccaccc cagcccctgc ggagccatgg        240
ctcggagtgg ctcctgcccg cacctgttgt gggacgtgag gaaaaggtcc cttgggctgg     300
aggacccgtc ccggctgagg agccgctacc tgggaagaag agaatttatc caaagattaa     360
aacttgaagc aactttaaat gtgcatgatg gctgtgttaa tacaatctgt tggaatgaca     420
ctggagaata tattttatct ggctctgatg acactaaact tgtaattagt aatccataca     480
gcagaaaggt tttgacaacc atccgttcag ggcatcgagc aaatatattt agtgcaaagt     540
ttttgccgtg cacagatgat aagcagattg tgtcttgctc tggagatgga gtcatatttt     600
atactaacat tgagcaagat gcagaaacta acagacagtg ccaatttacg tgccattatg     660
gaactactta tgagattatg actgtaccaa acgacccta cacctttctg tcctgtggtg     720
aagatggaac tgttaggtgg tttgacacac gcatcaaaac cagttgcaca aaagaagact     780
gtaaagatga tattttaatc aactgtaggc gtgctgccac atctgtggct atttgtcccc     840
cagtaccata ttaccttgct gtgggttgtt ctgacagctc agtacggatt tatgatcggc     900
gaatgctggg cacaagagct acagggaatt atgcaggccg aggaactact ggaatggttg     960
```

```
ctcgatttat accttctcat cttagtaaca aatcatgcag agtgacatca ctgtgttaca     1020
gtgaagatgg tcaagagatt cttgtcagtt attcttcaga ctacatctat cttttttgacc   1080
ccaaagatga tactgcacga gaacttaaaa ctccttctgc agaggagagg cgagaagagt    1140
tacgacagcc tccagttaag cgcttgagac ttcgtggtga ttggtcagat actggtccca   1200
gagcacggcc agaaagtgaa cgagaacgag atggagagca aagtcccaat gtgtcactga   1260
tgcagagaat gtctgatatg ttatcaaggt ggtttgaaga agcaagtgaa gttgcacaaa   1320
gcaacagagg aagaggaaga cctcggccca gaggtggaac aaatcagcca gatgtttcaa   1380
ctcttcctac ggttccatca agtcctaatt tggaagtgtg tgaaactgca atggatgtag   1440
acatgccagc tgcacttctt cagccttcta catcctctac agatccagtt caggctcagg    1500
cagccacagc cgcccataga agccctcgtt ccagctcgtt gctgtcttgc ccagacagtg   1560
aaccgaggca gtctgttgag gcgtctggac accatgcaca tcatcagtca gataacagta   1620
atgagaggct gagccccaaa ccagggacag gtgaacccgt tttaagtttg cactacagca   1680
cagaaggaac aactacaagc acaataaaac tgaactttac agatgaatgg agcagtacag   1740
cctcaagttc cagaggaaat gggagccatt gcaaatctga gggtcaggaa gaatgcttgg   1800
tccctccgag ctctgtgcag ccaccggaag gagacagtga acaagagct cctgaagaac    1860
tatcagagaa aggaacactt ccagaaaacc tcactcaaaa ccagatagat acagcacaac   1920
ttgataactt cccagctgag ccattggatt ctaactcagg agagaagaat aacccaagtc   1980
aggacagccc ttgtgggctt ccagaagaag gcactttgtc tgaaacagac agggagactt   2040
gtgagcaggc cagcactgag agtgctacca ggcatgctag caccaagcct gaactcccat   2100
cccagacaga agccattgag caggccagca ctgagagtgc taccaggcat accagtgcca   2160
atcctgaact cccatcccag acagaagcca tagcaccttt agctcatgaa gacccatctg   2220
ccagggactc tgctctccag gacacagatg acagcgatga tgatccggtc ttgatccctg   2280
gtgcaagata ccgaacagga cctggtgata gacgctccgc tgttgcccgc attcaggagt   2340
tcttcaggag gagaaaagaa aggaaagaaa tggaagagct ggatactttg aacattagga   2400
ggccactagt aaagatggtt tataagggcc accgcaactc ccggacaatg ataaaagaag   2460
ccaatttctg gggtgctaac tttgtaatga gcggttccga ttgtggccat atcttcatct   2520
gggaccggca cactgctgag catttgatgc ttctggaagc tgataatcat gtggtcaact   2580
gcctgcagcc ccatccgttt gacccaattc tagcctcatc tggcatagat tatgacataa   2640
agatctggtc gccactagaa gagtcaagaa ttttttaatcg aaaacttgct gatgaagtta   2700
taactcggaa tgaactcatg ctggaagaga ctcggaacac catcaccgtc ccagcctctt   2760
tcatgttgag gatgttggcg tcactgaatc atatccgagc tgaccgtctg gagggtgaca   2820
gatcagaagg ttcaggtcag gagaatgaaa atgaggatga agaataaaga actccttggc   2880
aagcacttag atgttctgag atttgtatac gacatttatt atatttttttt tctttacaga   2940
actttagtgc aatttaaggc tatgggtttt ttttttttttt tttttttttt ggagttcttc   3000
cctatttttgg ggataaccaa acattggttt ggaatgagtg tgtgcatgag ttgggagagt    3060
gtgtaaaaca aagtaagcaa aatgtttttt gaaaccttt gccgtgtatg gagtccaaaa    3120
aaaaaaaaaa aaaaaaaaaa aaagcaaagt gcaatacttc ctgaccctcc gctgtgggag   3180
cttggatcaa tgctgaagtc attttcattg tagtgaaaat gttggttcaa ataaatttct   3240
acacttgcca tttgcatgtt tgttgctttc taattaaaga tgttggttgc tttaagatat   3300
cctaaa                                                              3306
```

```
<210> SEQ ID NO 2
<211> LENGTH: 62
<212> TYPE: DNA
<213> ORGANISM: Mus musculus
<220> FEATURE:
<221> NAME/KEY: misc_feature
<222> LOCATION: (1)..(62)

<400> SEQUENCE: 2
gaagaagaga atttatccaa agattaaaac ttgaagcaac tttaaatgtg catgatggct    60
gt                                                                  62

<210> SEQ ID NO 3
<211> LENGTH: 22
<212> TYPE: DNA
<213> ORGANISM: Artificial Sequence
<220> FEATURE:
<223> OTHER INFORMATION: AU primer
<220> FEATURE:
<221> NAME/KEY: primer_bind
<222> LOCATION: (1)..(22)

<400> SEQUENCE: 3
aggtagattt ctgagtttga gg                                            22

<210> SEQ ID NO 4
<211> LENGTH: 25
<212> TYPE: DNA
<213> ORGANISM: Artificial Sequence
<220> FEATURE:
<223> OTHER INFORMATION: KU primer
<220> FEATURE:
<221> NAME/KEY: primer_bind
<222> LOCATION: (1)..(25)

<400> SEQUENCE: 4
gcttactttc atttatccct ctttg                                         25

<210> SEQ ID NO 5
<211> LENGTH: 23
<212> TYPE: DNA
<213> ORGANISM: Artificial Sequence
<220> FEATURE:
<223> OTHER INFORMATION: XD primer
<220> FEATURE:
<221> NAME/KEY: primer_bind
<222> LOCATION: (1)..(23)

<400> SEQUENCE: 5
gacattctta tcagctacac tag                                           23

<210> SEQ ID NO 6
<211> LENGTH: 876
<212> TYPE: PRT
<213> ORGANISM: Mus musculus
<220> FEATURE:
<221> NAME/KEY: MISC_FEATURE
<222> LOCATION: (1)..(876)

<400> SEQUENCE: 6

Met Ala Arg Ser Gly Ser Cys Pro His Leu Leu Trp Asp Val Arg Lys
1               5                   10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45
```

-continued

```
Val His Asp Gly Cys Val Asn Thr Ile Cys Trp Asn Asp Thr Gly Glu
     50                  55                  60

Tyr Ile Leu Ser Gly Ser Asp Thr Lys Leu Val Ile Ser Asn Pro
 65                  70                  75                  80

Tyr Ser Arg Lys Val Leu Thr Thr Ile Arg Ser Gly His Arg Ala Asn
                     85                  90                  95

Ile Phe Ser Ala Lys Phe Leu Pro Cys Thr Asp Asp Lys Gln Ile Val
                100                 105                 110

Ser Cys Ser Gly Asp Gly Val Ile Phe Tyr Thr Asn Ile Glu Gln Asp
             115                 120                 125

Ala Glu Thr Asn Arg Gln Cys Gln Phe Thr Cys His Tyr Gly Thr Thr
         130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                    165                 170                 175

Cys Thr Lys Glu Asp Cys Lys Asp Asp Ile Leu Ile Asn Cys Arg Arg
                180                 185                 190

Ala Ala Thr Ser Val Ala Ile Cys Pro Pro Val Pro Tyr Tyr Leu Ala
            195                 200                 205

Val Gly Cys Ser Asp Ser Ser Val Arg Ile Tyr Asp Arg Arg Met Leu
        210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Ser Asn Lys Ser Cys Arg Val
                    245                 250                 255

Thr Ser Leu Cys Tyr Ser Glu Asp Gly Gln Glu Ile Leu Val Ser Tyr
                260                 265                 270

Ser Ser Asp Tyr Ile Tyr Leu Phe Asp Pro Lys Asp Asp Thr Ala Arg
            275                 280                 285

Glu Leu Lys Thr Pro Ser Ala Glu Glu Arg Arg Glu Glu Leu Arg Gln
        290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
                    325                 330                 335

Pro Asn Val Ser Leu Met Gln Arg Met Ser Asp Met Leu Ser Arg Trp
                340                 345                 350

Phe Glu Glu Ala Ser Glu Val Ala Gln Ser Asn Arg Gly Arg Gly Arg
            355                 360                 365

Pro Arg Pro Arg Gly Gly Thr Asn Gln Pro Asp Val Ser Thr Leu Pro
        370                 375                 380

Thr Val Pro Ser Ser Pro Asn Leu Glu Val Cys Glu Thr Ala Met Asp
385                 390                 395                 400

Val Asp Met Pro Ala Ala Leu Leu Gln Pro Ser Thr Ser Ser Thr Asp
                    405                 410                 415

Pro Val Gln Ala Gln Ala Ala Thr Ala Ala Ile Glu Ser Pro Arg Ser
                420                 425                 430

Ser Ser Leu Leu Ser Cys Pro Asp Ser Glu Pro Arg Gln Ser Val Glu
            435                 440                 445

Ala Ser Gly His His Ala His His Gln Ser Asp Asn Ser Asn Glu Arg
        450                 455                 460

Leu Ser Pro Lys Pro Gly Thr Gly Glu Pro Val Leu Ser Leu His Tyr
465                 470                 475                 480
```

```
Ser Thr Glu Gly Thr Thr Thr Ser Thr Ile Lys Leu Asn Phe Thr Asp
            485                 490                 495
Glu Trp Ser Ser Thr Ala Ser Ser Arg Gly Asn Gly Ser His Cys
        500                 505                 510
Lys Ser Glu Gly Gln Glu Cys Leu Val Pro Ser Ser Val Gln
        515                 520                 525
Pro Pro Glu Gly Asp Ser Glu Thr Arg Ala Pro Glu Glu Leu Ser Glu
        530                 535                 540
Lys Gly Thr Leu Pro Glu Asn Leu Thr Gln Asn Gln Ile Asp Thr Ala
545                 550                 555                 560
Gln Leu Asp Asn Phe Pro Ala Glu Pro Leu Asp Ser Asn Ser Gly Glu
                565                 570                 575
Lys Asn Asn Pro Ser Gln Asp Ser Pro Cys Gly Leu Pro Glu Glu Gly
            580                 585                 590
Thr Leu Ser Glu Thr Asp Arg Glu Thr Cys Glu Gln Ala Ser Thr Glu
        595                 600                 605
Ser Ala Thr Arg His Ala Ser Thr Lys Pro Glu Leu Pro Ser Gln Thr
        610                 615                 620
Glu Ala Ile Glu Gln Ala Ser Thr Glu Ser Ala Thr Arg His Thr Ser
625                 630                 635                 640
Ala Asn Pro Glu Leu Pro Ser Gln Thr Glu Ala Ile Ala Pro Leu Ala
                645                 650                 655
His Glu Asp Pro Ser Ala Arg Asp Ser Ala Leu Gln Asp Thr Asp Asp
            660                 665                 670
Ser Asp Asp Asp Pro Val Leu Ile Pro Gly Ala Arg Tyr Arg Thr Gly
        675                 680                 685
Pro Gly Asp Arg Arg Ser Ala Val Ala Arg Ile Gln Glu Phe Phe Arg
        690                 695                 700
Arg Arg Lys Glu Arg Lys Glu Met Glu Glu Leu Asp Thr Leu Asn Ile
705                 710                 715                 720
Arg Arg Pro Leu Val Lys Met Val Tyr Lys Gly His Arg Asn Ser Arg
                725                 730                 735
Thr Met Ile Lys Glu Ala Asn Phe Trp Gly Ala Asn Phe Val Met Ser
            740                 745                 750
Gly Ser Asp Cys Gly His Ile Phe Ile Trp Asp Arg His Thr Ala Glu
        755                 760                 765
His Leu Met Leu Leu Glu Ala Asp Asn His Val Val Asn Cys Leu Gln
        770                 775                 780
Pro His Pro Phe Asp Pro Ile Leu Ala Ser Ser Gly Ile Asp Tyr Asp
785                 790                 795                 800
Ile Lys Ile Trp Ser Pro Leu Glu Glu Ser Arg Ile Phe Asn Arg Lys
                805                 810                 815
Leu Ala Asp Glu Val Ile Thr Arg Asn Glu Leu Met Leu Glu Glu Thr
            820                 825                 830
Arg Asn Thr Ile Thr Val Pro Ala Ser Phe Met Leu Arg Met Leu Ala
        835                 840                 845
Ser Leu Asn His Ile Arg Ala Asp Arg Leu Glu Gly Asp Arg Ser Glu
        850                 855                 860
Gly Ser Gly Gln Glu Asn Glu Asn Glu Asp Glu Glu
865                 870                 875

<210> SEQ ID NO 7
<211> LENGTH: 23
<212> TYPE: PRT
```

```
-continued
<213> ORGANISM: Mus musculus
<220> FEATURE:
<221> NAME/KEY: MISC_FEATURE
<222> LOCATION: (1)..(23)

<400> SEQUENCE: 7

Asp Arg Arg Ser Ala Val Ala Arg Ile Gln Glu Phe Phe Arg Arg Arg
1               5                   10                  15

Lys Glu Arg Lys Glu Met Glu
            20
```